(12) United States Patent
Kimura et al.

(10) Patent No.: US 6,303,375 B1
(45) Date of Patent: Oct. 16, 2001

(54) CELL SUPPORTING MATRIX, CELL CULTURE DEVICE, AND FLUID TREATING DEVICE

(75) Inventors: Tetsuhiro Kimura; Norifumi Tokunaga; Yoshitaka Omura, all of Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/338,382

(22) Filed: Jun. 23, 1999

(30) Foreign Application Priority Data

Jun. 23, 1998 (JP) .................................................. 10-192390

(51) Int. Cl.$^7$ ................................ C12N 5/00; C12N 5/06; C12N 5/08; C12N 11/02; C12N 11/08
(52) U.S. Cl. ......................... 435/395; 435/177; 435/180; 435/396; 435/397; 435/401; 435/262.5
(58) Field of Search .................................... 435/174, 177, 435/180, 182, 395, 396, 397, 401, 262.5

(56) References Cited

U.S. PATENT DOCUMENTS

| | | | |
|---|---|---|---|
| 4,440,853 | * | 4/1984 | Michaels et al. ....................... 435/68 |
| 5,071,747 | * | 12/1991 | Hough et al. ........................... 435/41 |

FOREIGN PATENT DOCUMENTS

| | | |
|---|---|---|
| 0408462B1 | 6/1995 | (EP) . |
| 5-76364 A | 3/1993 | (JP) . |
| 06153905 A | 6/1994 | (JP) . |
| 06277050 A | 10/1994 | (JP) . |
| 06284883 A | 10/1994 | (JP) . |
| 06335382 A | 12/1994 | (JP) . |
| 7-46988 B | 5/1995 | (JP) . |
| 8-25886 B | 3/1996 | (JP) . |
| 11046759 A | 2/1999 | (JP) . |
| WO 93/16171 | 8/1993 | (WO) . |
| WO 96/30492 | 10/1996 | (WO) . |
| WO 97/12960 | 4/1997 | (WO) . |

OTHER PUBLICATIONS

Nakazawa, K. et al, Artificial Organs, vol. 27(1), pp. 222–226, 1998.

Miyoshi, H. et al, Artificial Organs, vol. 23(2), pp. 479–484, 1994.

Ijima, H. et al, Artificial Organs, vol. 23(2), pp. 463–468, 1994.

Matsushita, T. et al, Artificial Organs, vol. 24(3), pp. 815–820, 1995.

Miyoshi, H. et al, Artificial Organs, vol. 24 (3), pp. 744–748, 1995.

Yanagi et al., *ASAIO Journal 1998*, pp. M436–440.

Kora et al., Chapter 10 entitled "Mechanism of Leukocyte Removal By Porous Material," pp. 119–129, 1992.

Matsushita et al., *Applied Microbiology and Biotechnology*, 33:287–290 (1990).

Matsushita et al., *Applied Microbilogy and Biotechnology*, 35:159–164 (1991).

Ohshima et al., *Artificial Organs*, 21(11):1169–1176 (1997).

Gutsche et al., Biomaterials, vol. 17, No. 3, Feb. 1, 1996, pp. 387–393, XP004032805.

* cited by examiner

*Primary Examiner*—David M. Naff
(74) *Attorney, Agent, or Firm*—Burns, Doane, Swecker & Mathis, LLP (57) ABSTRACT

A matrix for supporting cells such as animal cells is provided that enables cells to be supported at high efficiency and density in a short period. The matrix contains a plurality of cone shaped pores having an average diameter opening in an upstream surface of the matrix of from 500 to 1500 μm. The diameter decreases from the upstream surface to a downstream surface, and the average diameter of the cone shaped pores in the whole matrix is from 100 to 1000 μm. The matrix also contains a plurality of communicating pores that communicate with the cone shaped pores and with each other. These pores have an average diameter of from 5 to 100 μm, and the diameter decreases from a pore opening positioned near one surface of the matrix or near an interior surface of the cone shaped pores to a pore opening positioned remote from the surfaces. The matrix may also contain a plurality of column shaped pores having an average diameter of 100 to 1000 μm. A porous skin layer having an average pore size smaller than the average pore size of the communicating pores may be on the downstream surface, and the matrix may be made of polyurethane.

9 Claims, 8 Drawing Sheets

CELL SUPPORTING MATRIX, CELL CULTURE DEVICE, AND FLUID TREATING DEVICE

BACKGROUND OF THE INVENTION

This invention relates to a cell supporting matrix for supporting cells, a cell culture device and a fluid treating device wherein such cell supporting matrix is used.

Cell cultivation has been conducted by known processes such as those utilizing microcarriers, hollow fibers, porous matrices, and microcapsules.

Among these, attention has focused on the cell culture process wherein a cell suspension is injected into a matrix having a three dimensional porous structure and to the process wherein such matrix is impregnated with the cell suspension for immobilization and culturing of the cells.

In the perfusion culture utilizing such cell supporting matrix, flow paths for the liquid culture medium are necessary, and various improvements have been disclosed. Exemplary such improvements include provision of capillaries having a diameter of 1.5 mm at an interval of 3 mm in the matrix as disclosed in Ijima et al., Artificial Organs vol. 23, page 463, 1994 (in Japanese) and use of some matrices in the form of 2 mm cubic blocks as disclosed in Ohshima et al., Artificial Organs, vol. 21, page 1169, 1997.

When cell seeding by plain sedimentation precipitation is conducted by such methods, percentage of the cells immobilized is extremely low in the range of 10 to 30%, and efficient cell immobilization is not realized by such processes. Such processes, therefore, have proved impractical.

An improvement has been proposed wherein the matrix filled with the cells is subsequently subjected to centrifugation so that the cells may move in the matrix in the exterior direction, and the percentage of the cells immobilized has been thereby increased. In this process, the percentage of the cells immobilized has been increased to 80%.

This process, however, is impractical since a prolonged period as well as troublesome handling are required before the cell immobilization.

As described above, no technique has been so far provided which is capable of immobilizing and culturing the cells at a high density in a simple, efficient manner and in a short period.

SUMMARY OF THE INVENTION

In view of such situation, an object of the present invention is to provide a cell supporting matrix which is capable of efficiently supporting the cells at a high density in a short period. Another object of the invention is to provide a cell culture device and a fluid treating device utilizing such cell supporting matrix.

Such objects of the invention are achieved by the present invention according to (1) to (17), below.

(1) A cell supporting matrix for supporting cells, said cell supporting matrix having formed therein
   a plurality of large pores, and
   a plurality of communicating pores whose pore size decreases from one surface of the cell supporting matrix and from interior surface of said pore to the interior of the cell supporting matrix.

(2) A cell supporting matrix according to the above (1) wherein said communicating pores have a pore size ranging from below to beyond the cell size of the cells to be immobilized in the cell supporting matrix.

(3) A cell supporting matrix for immobilizing cells wherein
   said cell supporting matrix has a plurality of large pores and a plurality of communicating pores formed therein, and
   said communicating pores have a pore size ranging from below to beyond the size of the cells to be immobilized in the cell supporting matrix.

(4) A cell supporting matrix according to any one of the above (1) to (3) wherein said large pores include pores which open at said one surface of the cell supporting matrix.

(5) A cell supporting matrix according to any one of the above (1) to (4) wherein said large pores have finger-like structure.

(6) A cell supporting matrix according to any one of the above (1) to (5) wherein said macro pores have an average pore size in the range of from 100 to 1000 μm.

(7) A cell supporting matrix according to any one of the above (1) to (6) wherein said communicating pores have an average pore size in the range of from 5 to 100 μm.

(8) A cell supporting matrix according to any one of the above (1) to (7) wherein said communicating pores has have a maximum pore size in the range of from 30 to 200 μm.

(9) A cell supporting matrix according to any one of the above (1) to (8) wherein said communicating pores have a minimum pore size in the range of from 0.1 to 10 μm.

(10) A cell supporting matrix according to any one of the above (1) to (9) wherein said cell supporting matrix further comprises a porous skin layer on the surface other than said one surface wherein said large pores have their opening.

(11) A cell supporting matrix according to any one of the above (1) to (10) wherein said skin layer has an average pore size smaller than said average pore size of said communicating pores.

(12) A cell supporting matrix according to any one of the above (1) to (11) wherein said matrix has elasticity.

(13) A cell supporting matrix according to any one of the above (1) to (12) wherein said cell is an animal cell.

(14) A cell culture device which has the cell supporting matrix of any one of the above (1) to (13), and wherein the cells are immobilized and cultured in said cell supporting matrix.

(15) A cell culture device according to the above (14) wherein said device has a faculty for recovering the product from said cells.

(16) A fluid treating device which has the cell supporting matrix of any one of the above (1) to (13), and wherein said device is used by passing a fluid through said cell supporting matrix and treating the fluid by utilizing the metabolic or biosynthetic function of the cells supported on said cell supporting matrix.

(17) A fluid treating device according to the above (16) wherein said device functions as a bioartificial liver.

DETAILED DESCRIPTION OF THE INVENTION

Next, the present invention is described in further detail by referring to the preferred embodiments shown in the drawings.

Figure 1:
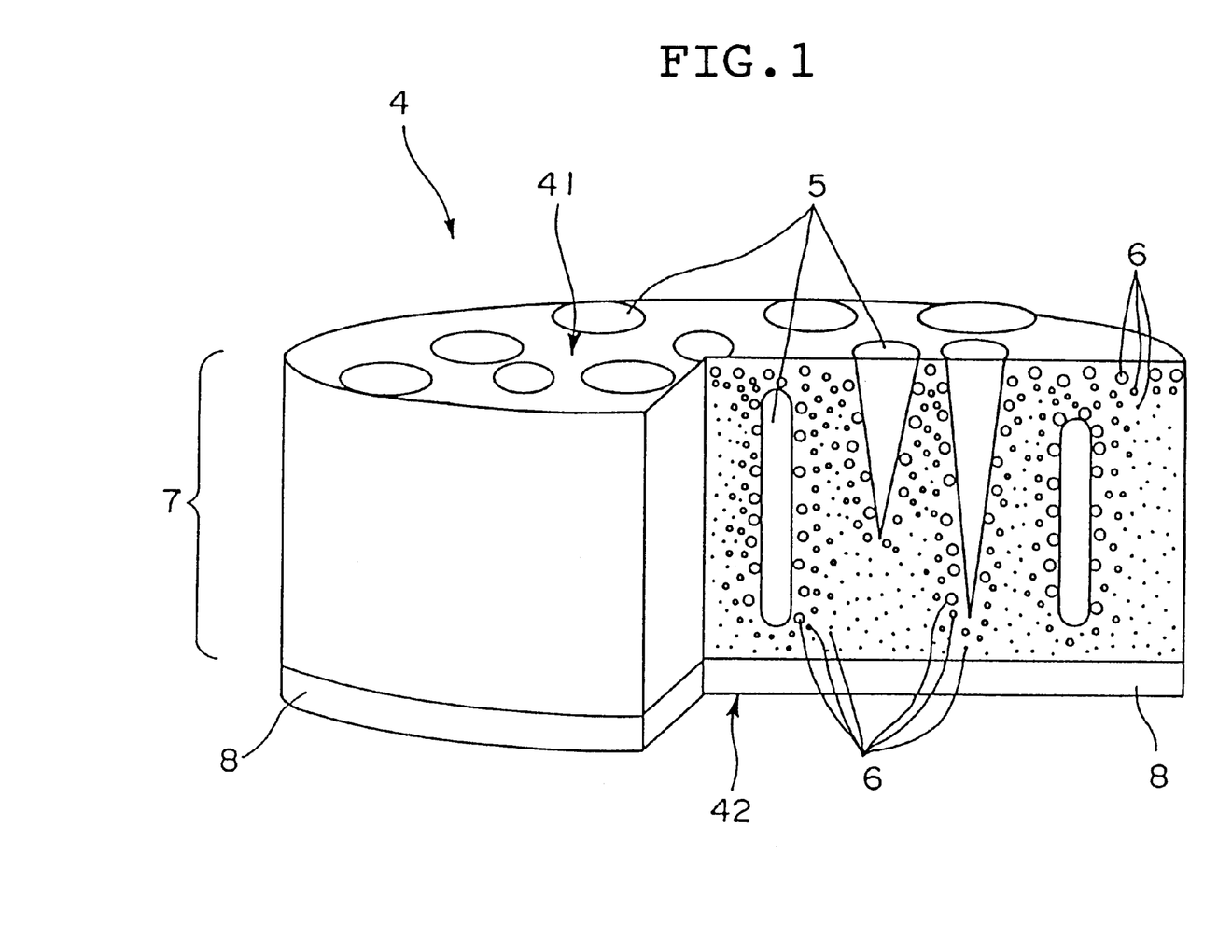
FIG. 1 is a schematic view showing cross section of an embodiment of the cell supporting matrix of the present invention.
Figure 2:
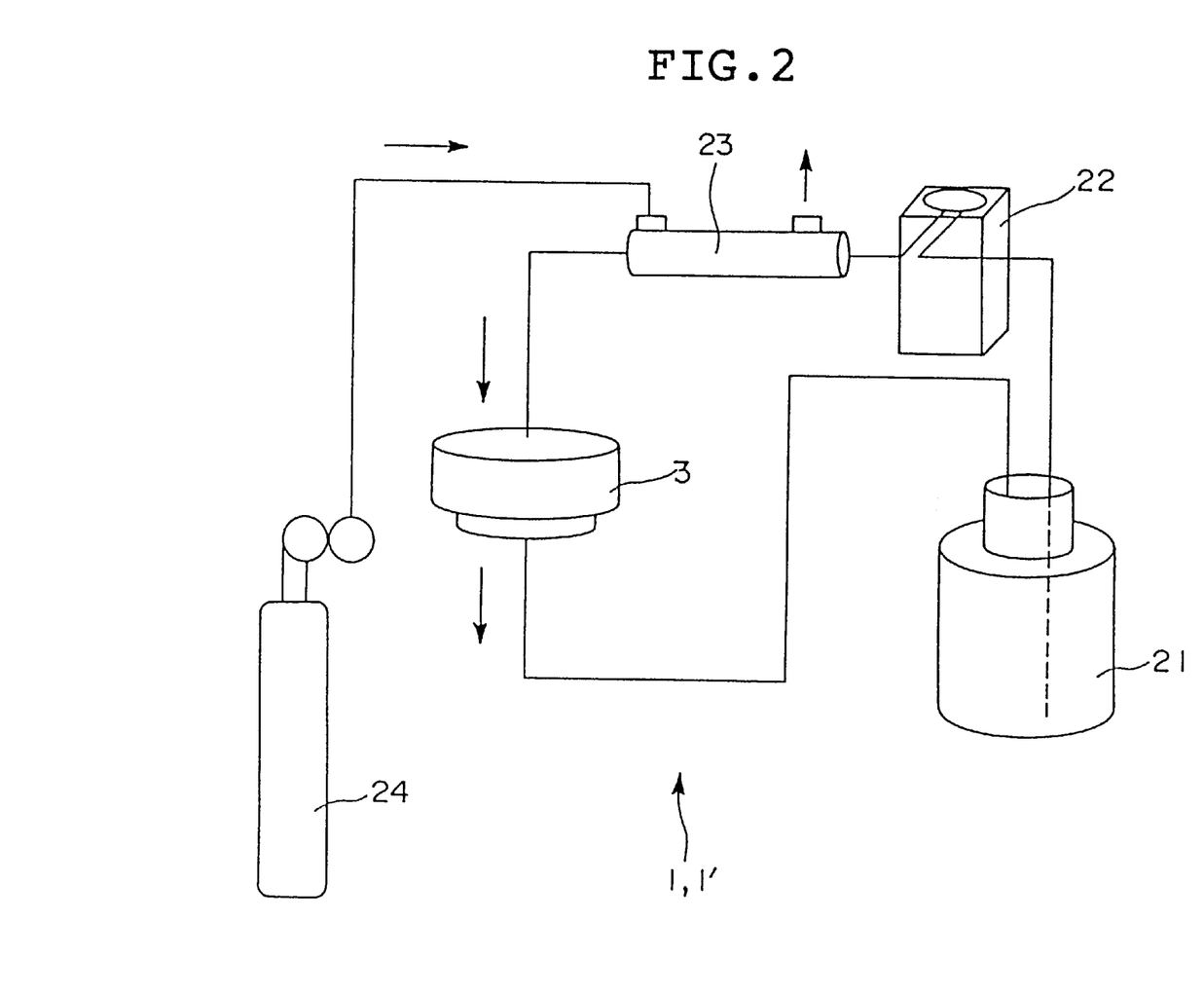
FIG. 2 is a schematic circuit diagram of an embodiment of the cell culture device according to the present invention.

FIG. 1 is a schematic view showing cross section of an embodiment of the cell supporting matrix of the present invention. FIG. 2 is a schematic circuit diagram of an embodiment of the cell culture device of the present invention.

As shown in FIG. 1, a cell supporting matrix 4 comprises a cell supporting layer 7 and a skin layer 8.

In the cell supporting matrix 4, the liquid passing through the matrix flows, in principle, from the cell supporting layer 7 to the skin layer 8. The side of the cell supporting layer 7 in the cell supporting matrix 4 is hereinafter referred to as the "upstream end" and the opposite side of the cell supporting matrix 4, namely, the side of the skin layer 8 is hereinafter referred to as the "downstream end".

The cell supporting layer 7 has formed therein a plurality of large pores 5 having a larger pore size and a plurality of communicating pores 6 having a smaller pore size.

The large pores 5 has finger-like structure as a column, a cone or other form in the cell supporting matrix 4. The longitudinal axis of the large pores 5 extends substantially in the flow direction of the fluid passing through the cell supporting matrix 4. The large pore 5 does not extend through the cell supporting matrix 4.

The large pores 5 serve the flow path of the fluid passing through the cell supporting matrix 4, and when a cell suspension is allowed to flow through the cell supporting matrix 4, the large pores 5 are estimated to serve the flow path of the cells.

Some of the large pores 5 located near the upstream end surface 41 of the matrix has an open end on the upstream end surface 41. In the case of such large pores 5 having the open end, the upstream end surface 41 is continuous with the interior surface of the large pore 5. When the cell suspension is allowed to flow from the upstream side of the cell supporting matrix 4, the large pores 5 having such an open end facilitate the advancement of the cells into the interior of the cell supporting matrix 4.

The average pore size of the opening of the large pores 5 in the upstream end surface 41 is not particularly limited, and depends on the size and the type (nature) of the target cell. In view of facilitating the filling of the cells in the matrix, the average pore size of the opening of the large pores 5 is preferably in the range of from about 100 to about 2000 μm, and more preferably in the range of about 500 to about 1500 μm.

The pore size of the large pores 5 may preferably decrease from the upstream end 41 toward the downstream end 42 of the cell supporting matrix 4 since uniform distribution of the cells in the cell supporting layer 7 is facilitated by such pore configuration.

The average pore size of the large pores 5 is not particularly limited. The average pore size, however, is preferably in the range of from about 100 to about 1000 μm, and more preferably in the range of about 100 to 500 μm. When the average pore size is below the lower limit of such range, the cell suspension may not smoothly flow through the cell supporting matrix 4, and introduction of the cells into the deep interior of the cell supporting matrix 4 may become difficult. On the other hand, when the average pore size is beyond the upper limit of such range, substantial volume of the cell supporting layer 7 will be reduced and the matrix may detract from sufficient strength to support of the target cells.

The communicating pore 6 is in communication with the adjacent communicating pore 6, and the communicating pores 6 as a whole constitute a three dimensional pore network.

The communicating pores 6 serve the flow path of the fluid passing through the cell supporting matrix 4, and at the same time, play the role of entrapping the target cells (cells to be immobilized and supported) by the features as described below.

The communicating pores 6 are formed such that the pore size decreases from the upstream end surface 41 of the cell supporting matrix or from interior surface of said large pore 5 (hereinafter generally referred to as the surface) toward the interior of the cell supporting matrix, that is, as the communicating pore 6 advances from the surface.

In addition, the pore size of the communicating pores 6 may range from beyond to below the size of the target cells. The communicating pores 6 having a pore size in excess of the size of the target cells to be filled in the matrix facilitate free passage of the cells therethrough while the communicating pores 6 having a pore size smaller than the size of the target cells facilitate entrapment of the cells therein.

Therefore, the passage of the cells through the communicating pores 6 is facilitated in the region near the surface, and the cells are less likely to be entrapped in such region. As the cells advance into the matrix, the cells become more likely to be entrapped by the communicating pores 6 of the reduced pore size.

The degree in the reduction of the pore size of communicating pores 6 may preferably vary in accordance with the position of the communicating pores 6 in the cell supporting layer 7 so that the sites of the target cell entrapment are not concentrated in the area at a certain distance from said surface, and will be distributed widely and uniformly throughout the cell supporting matrix 4. It is believed that the flow path of the fluid passing through the communicating pores 6 is consequently maintained even after the entrapment of the target cells in the communicating pores 6, and uniform, rapid passage of the fluid through the cell supporting matrix 4 is ensured after the supporting of the cells in the cell supporting matrix 4. It is also estimated that a uniform supporting of a larger number of target cells in the cell supporting matrix 4, namely, supporting of the target cells at a higher density is thereby enabled.

Average pore size of the communicating pores 6 is not particularly limited. The average pore size, however, is preferably in the range of from 5 to 100 μm, and more preferably in the range of from 10 to 70 μm. When the average pore size is in excess of the upper limit of such range, percentage of the target cells entrapped may become insufficient. On the other hand, when the average pore size is below the lower limit of such range, there is some risk that the cells may not reach sufficient depth in the communicating pores 6 or the flow path for the fluid passing through the cell supporting matrix 4 may become insufficient.

The maximum pore size of the communicating pores 6 is not particularly limited. The maximum pore size, however, is preferably in the range of from 30 to 200 μm, and more preferably in the range of from 50 to 150 μm. The term "maximum pore size" used herein does not indicate the maximum pore size of all the existing communicating pores 6, but the maximum pore size after excluding the pores having a deviation of 5% or more from the pore size profile.

The minimum pore size of the communicating pores 6 is not particularly limited. The minimum pore size, however, is preferably in the range of from 0.1 to 10 μm, and more preferably in the range of from 1 to 10 μm. The term "minimum pore size" used herein does not indicate the minimum pore size of all the existing communicating pores 6, but the minimum pore size after excluding the pores having a deviation of 5% or more from the pore size profile.

The material used for the cell support layer 7 may be any material which is porous and which is capable of supporting the cells. In view of the capability of entrapping the cells, the material used is preferably the one having elasticity, and in view of facilitating the fluid passage, the material used is preferably the one having hydrophilicity and water retaining ability. Furthermore, in view of stability, the material used is preferably the one which is less likely to be metabolized by the cells supported on the cell support layer 7. Exemplary materials are natural products and synthetic resin foams, the latter including polyurethane, polyvinylalcohol, and the like.

The cell supporting layer 7 as described above has very high cell entrapping capability by itself. Further provision of the skin layer 8 enables prevention of the cell leakage from the cell supporting matrix 4 even if a small number of the cells should escape from the cell supporting layer 7.

The skin layer 8 comprises a porous material. The skin layer 8 may preferably have an average pore size which is smaller than that of the communicating pores 6 in view of efficient prevention of the cell leakage from the cell support material 4 and reliable supporting of the target cells in the cell support material 4.

The average pore size of the skin layer 8 is not particularly limited. The average pore size, however, is preferably in the range of about 0.2 μm to about 35 μm, more preferably from about 1 μm to about 10 μm, and still more preferably from about 1 μm to about 5 μm. The average pore size in excess of the upper limit of such range is associated with the risk of inefficient prevention of the cell leakage, and the average pore size below the lower limit of such range is associated with the risk of insufficient flow passage of the fluid through the skin layer 8.

The thickness of the skin layer 8 is not particularly limited. The thickness, however, is preferably in the range of from about 10 μm to about 2 mm, and more preferably, from about 100 μm to about 1 mm. When the thickness is in excess of the upper limit of such range, smooth flow of the fluid through the cell supporting matrix 4 may be prevented depending on the pore size of the skin layer 8. When the thickness is below the lower limit of such range, the skin layer 8 may not prove its full worth.

The skin layer 8 may comprise a material the same as the one used for the cell supporting layer 7.

The skin layer 8 may be integrally formed with the cell supporting layer 7, or separately formed with a different matter and adhered to the cell supporting layer 7 afterwards.

In the case of the cell supporting matrix 4 wherein the cell supporting layer 7 and the skin layer 8 are integrally formed, production is simple, and the cell supporting layer 7 and the skin layer 8 are strongly adhered to each other.

In the case of the cell supporting matrix 4 wherein the cell supporting layer 7 and the skin layer 8 are integrally formed, control of the pore size is facilitated.

It should be noted that the cell supporting matrix 4 may comprise at least one additional layer between the cell supporting layer 7 and the skin layer 8 or in the downstream of the cell supporting layer 7 from the skin layer 8.

It should also be noted that the skin layer 8 may be provided separately from the cell supporting layer 7. In other words, the skin layer 8 may be provided separately in the downstream of the cell supporting layer 7, and at some distance from the cell supporting layer 7.

In addition, the cell supporting matrix 4 may not necessary include the skin layer 8.

In particular, in the case wherein a plurality of cell support matrices 4 are stacked and accommodated in the cell supporting module 3 or the like as will be described below, supporting of the target cells at a more uniform distribution by the cell support matrices from the upstream end to the downstream end will be realized by using the cell support matrices 4 free from the skin layer 8 except for the matrix in the downstream end, and the number of cells supported in the cell supporting module 3 can be thus increased.

The cell supporting matrix 4 is preferably of columnar shape, since a cell supporting matrix 4 of columnar shape is capable of supporting the target cells within its interior at a higher uniformity. The shape of the cell supporting matrix 4 is not limited to such columnar shape, and the cell supporting matrix 4 may be advantageously used by selecting a shape adapted for the cell supporting module 3 in which the cell supporting matrix 4 is to be accommodated.

The thickness of the cell supporting matrix 4 is not particularly limited. The thickness, however, is preferably in the range of from about 0.1 to about 300 mm, and more preferably, from about 0.5 mm to about 10 mm. When the thickness is in excess of the upper limit of such range, the target cells may not be adequately filled in the matrix. When the thickness is below the lower limit of such range, the percentage of the target cells entrapped may become insufficient.

The cell supporting matrix having the structure as described above may be produced by foaming the material of the cell supporting layer 7. A process wherein the cell supporting layer 7 and the skin layer 8 are integrally formed is hereinafter described as a preferred embodiment of the present invention.

A composition comprising the material of the cell supporting layer 7, for example polyurethane, a pore forming agent, a nucleating agent, and a solvent for the polyurethane is first deaerated under reduced pressure, poured into a mold, covered with a nonwoven fabric, and allowed to gelate (solidify) in water for shaping.

The solvent for the material of the cell supporting layer 7 may vary in accordance with the material of the cell supporting layer 7 employed. Exemplary solvents include dimethylformamide, dimethylsulfoxide, acetone, dioxane, methylcellosolve acetate, tetrahydrofuran, ethyl alcohol, methyl alcohol, methyl ethyl ketone, phenol, formic acid, an aromatic hydrocarbon, a chlorinated hydrocarbon, a fluorinated alcohol.

In the present invention, the material of the cell supporting layer 7 (hereinafter referred to as polyurethane for convenience) is preferably dissolved in the solvent to a relatively low concentration of up to about 20% by weight. The speed of the gelation is thereby reduced, and the desired pore size profile of the pores, and in particular, the desired diameter profile of the communicating pores is thereby realized.

The pore forming agent used may comprise any high molecular weight compound which dissolves in or which is swelled by water and/or alcohol. Exemplary pore forming agents include polyvinyl alcohol, polyvinyl pyrrolidone, methylcellulose, polyeter, polysaccharide, polyacrylamide, and polyacrylic acid or its salt, which may be used either alone or in combination of two or more. Among these the preferred is methylcellulose.

The pore forming agent is generally used in an amount of 30 to 200 parts by weight, and preferably in an amount of 70 to 120 parts by weight per 100 parts by weight of polyurethane.

The nucleating agent used may comprise a compound which does not dissolve in the solvent for polyurethane, which uniformly mixes with the pore forming agent, which dissolves in water and/or alcohol, and which acts as an agent for regulating the pore size. Exemplary such nucleating agents include arginic acid, carboxy methyl cellulose, polyacrylate, a starch, dextrin, and inorganic salts such as chloride or sulfate of sodium, potassium, calcium, strontium, and aluminum. Among these, the preferred is calcium chloride.

The nucleating agent is generally used in an amount of at least 5 parts by weight, and preferably in an amount of at least 30 parts by weight per 100 parts by weight of polyurethane.

In the present invention, use of the pore forming agent in combination with the nucleating agent, and in particular, use of the nucleating agent in the amount as described above has enabled to provide the cell supporting layer 7 having the final structure wherein two types of pores having different pore size profiles, namely, the large pores and the communicating pores are formed.

As described above, the composition deaerated under the reduced pressure is poured into a mold and allowed to undergo gelation to obtain the shaped cell supporting layer 7. In such process, it is preferable that the cell supporting layer 7 having a substantial thickness is gelated, and therefore, the mold used may generally have a depth of 9 mm or more, and a typical depth of the mold is about 15 mm. The mold may comprise any material as long as the material is water permeable. The mold material, however, is preferably a nonwoven fabric since the use of a nonwoven fabric for the mold enables to form the skin layer 8 at the contact face of the cell supporting layer 7 with the mold face. It is estimated that the communication pores of the present invention having the desired pore size profile are realized by such gelation of the cell supporting layer 7 of substantial thickness which is covered with a water permeable material.

The cell supporting matrix 4 of the present invention can support cells such as animal cells, plant cells, and bacterial cells (including the transformant cells produced by genetic engineering, cell fusion and the like). Use of the cell supporting matrix 4 of the present invention has enabled a convenient supporting and cultivation at a high entrapment rate of the animal cells whose cultivation at a high density had been difficult (and in particular, the cultivation of attachment animal cells which required a substrate for attachment thereto, including those constituting organs such as hepatocyte, lung cell, kidney cell, ovary cell, islet cell, neurocyte, pituicyte, thyroid cell, adrenocortical cell; neuroblast, fibroblast, epitheliocyte, and endothelial cell). Use of the cell supporting matrix 4 of the present invention has also enabled cultivation of suspending cells such as hemopoietic stem cell and stromal cell in a manner far more convenient and at an entrapping rate much higher than the conventional matrices.

When the suspension of the target cells is passed through the cell supporting matrix 4, the target cells are entrapped in the communicating pores 6 as the suspension passes through the cell supporting layer 7. In other words, the target cells can be entrapped and loaded on the cell supporting matrix 4 by merely passing the suspension of the target cells from the upstream end of the cell supporting matrix 4.

As described above, use of the cell supporting matrix 4 of the present invention enables convenient loading of the cells on the matrix with no special operation, and the cells can be loaded on the matrix in a quite short period. Since a large number of cells are loaded on the matrix in a short period, the cell loading procedure can be completed at a high efficiency.

The passage of the fluid through the cell supporting matrix can be accomplished, for example, by gravitational flow of the cell suspension through the matrix from the upstream end, or by using a constant flow rate pump such as a syringe pump or an aspirator.

The cell supporting matrix 4 as described above can be used in a cell culture device, a fluid treating device, and the like, and use of the cell supporting matrix 4 in such device enables cell cultivation and treatment of the fluid by means of the cell cultivation in a convenient manner.

Also realized in the present invention is a high percentage of cell immobilization. For example, a percentage of cell immobilization of at least 80% and preferably at least 95% is realized even when the cells are immobilized by natural gravitational cell seeding.

Next, cell culture device 1 utilizing the cell supporting matrix 4 is described.

As shown in FIG. 2, the cell culture device 1 has a perfusion line and a gas line for gas addition. The perfusion line comprises a reservoir 21, a pump 22, a gas addition means 23, and a cell supporting module 3. The gas line is connected to a compressed-gas cylinder 24 at one end and to the gas addition means 23 at the other end.

The reservoir 21 stores the perfusate such as the liquid culture medium flowing through the cell culture device 1.

The liquid culture medium used as the perfusate in the present invention is not limited to any particular type as long as the liquid culture medium is the one which can be used for the cell cultivation. Any known liquid culture medium which is capable of proliferating or maintaining the cells may be employed including those containing the serum and those free from the serum.

The liquid culture medium which may be employed may also be the one containing a nutritious substance, namely, the substance which is taken into the cells and used as a metabolic substrate or a coenzyme. Exemplary such nutritious substances include sugars such as glucose; trace essential metals such as Fe, Zn, Se, Cu, Mn, Mo and V; essential amino acids; non-essential amino acids such as serine and glycine; and water-soluble vitamins.

The liquid culture medium employed may also contain a growth factor such as EGF, HGF or insulin; or an antibiotic such as penicillin G or streptomycin.

A liquid culture medium which is preferably employed in the present invention is the one which contains hemoglobin and/or a heme complex as an oxygen transporting agent. In such a case, the hemoglobin and/or the heme complex is preferably encapsulated in a liposome. The concentration of the final concentration of the hemoglobin and/or the heme complex in such liquid culture medium is preferably in the range of from 1 to 12% by weight, and more preferably, from 3 to 9% by weight although the concentration should be determined in accordance with the type of the cell cultivated. The pH is preferably adjusted to the range of from 7.2 to 7.4, and the crystalloid osmotic pressure is preferably adjusted to the range of from 250 to 300 Osm/kg.

Such liquid culture medium containing the hemoglobin and/or the heme complex (hereinafter referred to as "high oxygen liquid culture medium") already contain a substantial amount of oxygen at atmospheric pressure, and therefore, such liquid culture medium is quite appropriate for use in the primary culture, in particular, in the primary culture of hepatocytes, hemangioendotherial cells, bone cells, bone marrow cells, and the like immediately after their isolation from the body. Usually, the cells immediately after the isolation from the body is greatly damaged, and a larger amount of oxygen is required in the primary stage culture of such damaged cells. Use of the high oxygen liquid culture medium is highly adapted for such primary culture.

It should be noted that the high oxygen liquid culture medium as described above can be used for the primary culture medium when the cell supporting matrix of the present invention is used in the bioartificial organ as will be described below, for example, in a bioartificial organ such as hybrid artificial liver.

More illustratively, when hepatocytes isolated from a human or a pig is used in the bioartificial organ as will be described below, for example, in a hybrid artificial liver utilizing hepatocytes, the high oxygen liquid culture medium as described above can be used for the primary culture medium until the cells become stabilized. In addition, the cells are incorporated in the hybrid artificial liver at a high density, and therefore, the high oxygen liquid culture medium as described above is useful as a means for supplying the oxygen to the hybrid artificial liver.

In an exemplary hybrid artificial liver of modular type, the high oxygen liquid culture medium as described above may be used for perfusion through the cells supported on the module after increasing the oxygen partial pressure of the liquid culture medium by passing the liquid culture medium through a gas exchanger provided on the line.

The pump 22 is provided for the purpose of circulating the parfusate through the perfusion line of the cell culture device 1. An exemplary pump 22 is a roller pump.

The gas addition means 23 is a means which adds oxygen (or an oxygen-containing gas mixture) supplied from the compressed-gas cylinder to the perfusate, for example, through hollow fiber membranes provide in the gas addition means. The oxygenated perfusate contacts with the cells on the cell supporting matrix 4 in the cell supporting module 3, and the cells are thereby supplied with the oxygen. It should be noted that the gas supplied from the compressed-gas cylinder 24 to the gas addition means 23 is not limited to oxygen, and other gases such as carbon dioxide, nitrogen, ethylene, and mixtures thereof can be supplied from the compressed-gas cylinder 24 to the gas addition means 23.

The cell supporting module 3 accommodates therein at least one cell supporting matrix 4, and the cells supported therein grow and proliferate to undergo various activities including metabolism and biosynthesis.

The cell supporting module 3 may further comprise an optional filter means in its interior and in the downstream of the cell supporting matrix 4. Exemplary filter means include a mesh, a paper, a woven fabric, a non-woven fabric, a porous membrane, a porous plate, and various filters (such as a membrane filter). Provision of such filter means facilitates a smooth fluid flow in the cell supporting module 3 and ensures prevention of the cell leakage from the cell supporting module 3 to its downstream.

Such constitution of the perfusion line provides the cell culture device 1 with an improved seal, and contamination of the cell culture device 1 by harmful bacteria is thereby prevented.

Next, the method for using the cell culture device 1 (i.e. operation of the cell culture device 1) is described.

In the use of the cell culture device 1, the cell supporting matrix 4 having the cells loaded thereon is first packed in the cell supporting module 3. It should be noted that it is also possible to load the cells on the cell supporting matrix 4 after placing the cell supporting matrix 4 in the cell supporting module 3.

Next, the pump 22 is actuated so that the perfusate stored in the reservoir 21 may flow through the cell culture device 1.

The perfusate then leaves the reservoir 21 to arrive at the gas addition means 23 where it is oxygenated, and at the same time, the perfusate is purged with unnecessary gases such as carbon dioxide which had dissolved in the perfusate.

The oxygenated perfusate reaches the cell supporting module 3 and passes through the cell supporting matrix 4 to supply the cells supported thereon with oxygen and other nutrients required for their life processes.

The perfusate which passed through the cell supporting module 3 then returns to the reservoir 21 where it is stored.

As described above, the perfusate passes through the cell supporting matrix 4 to supply the cells supported thereon with oxygen and other nutrients, and cultivation of the target cells is thereby enabled.

The cell culture device 1 may further comprise a mechanism for collecting the product produced by the cells supported on the cell supporting matrix 4 such as a protein, a saccharide, a hormone or other chemical substance either during the cultivation or after the completion of the cultivation. In an exemplary mechanism, the product is removed through filtration or adsorption by means of a filter (a product removing means) provided in the perfusion line or in the branch or bypass of the perfusion line. In another mechanism, the perfusate is periodically subjected to washing, filtration or other treatment, or the perfusate is periodically exchanged for the collection of the product.

Such mechanism provided with the cell culture device enables continuous cultivation or facilitate the cell cultivation.

The device shown in FIG. 2 may also be used as a fluid treating device 1'. In other words, the fluid passing through the cell supporting matrix 4 can be treated by utilizing the metabolic or biosynthetic function of the cells supported on the cell supporting matrix 4.

For example, the liquid treatment device 1' can function as a bioartificial organ such as a bioartificial liver by loading the cells constituting an organ such as hepatocytes in the cell supporting matrix 4.

In such a case, a fluid such as plasma and blood can be treated by using such fluid for the perfusate.

The fluid treating device 1' can also be used for synthesizing, decomposing, or treating a particular substance by immobilizing a particular type of cells in the cell supporting matrix 4. In other words, the fluid treating device 1' can function as a bioreactor.

In such a case, the fluid treated by the fluid treating device 1' may be obtained as the product.

The present invention has been described by referring to the embodiments shown in the drawings, which by no means limit the scope of the present invention.

The cell supporting matrix 4 having the cells immobilized therein can also be used for a static culture.

Furthermore, the cell supporting matrix 4 having the cells immobilized therein can be used for applications other than those mentioned above, for example, for production of viruses.

Next, the present invention is described in further detail by referring to Examples of the present invention and Comparative Examples which by no means limit the scope of the present invention.

EXAMPLES

1. Production of Cell Supporting Matrix

[1.1] Preparation of material for the cell supporting matrix

Polyurethane (PU) was added to N-methyl-2-pyrrolidone (NMP, solvent) to a concentration of 11% by weight. To this solution was added calcium chloride ($CaCl_2$, nucleating agent) to a concentration of 30 parts by weight per 100 parts by weight of the polyurethane.

Next, the solution was stirred at a rate of 1000 rpm for 6 hours in a water bath at a temperature of up to 40° C.

After stirring, the solution was allowed to stand for 8 hours or more. 800 g of the solution was added to the tank of a planetary mixer, and methyl cellulose (MC, pore forming agent) of the weight the same as the polyurethane in the solution was then added to the tank. The mixture was kneaded at a rate of 60 rpm and at a bath temperature of 60° C.

[1.2] Formation of the cell supporting matrix

The material of the cell supporting matrix immediately after the kneading was kept under reduced pressure for deaeration (degassing).

The deaerated material of the cell supporting matrix was introduced in a box made from a nonwoven fabric to a depth of 15 mm, and the upper surface was covered with the nonwoven fabric.

Next, the material was immersed in a water bath of 50° C. for about 2 hours for solidification. The bath temperature was reduced to room temperature and immersion was continued for another 16 hours or more to further promote the solidification.

It is likely that the large pores and the communication pores were formed in the course of the immersion by dissolution of the nucleating agent and the pore forming agent.

[1.3] Washing and slicing of the cell supporting matrix

The nonwoven fabric was removed from the solidified cell supporting matrix material, and the material was rinsed under running water with a roll squeezer.

The material was then dried at 60° C.

After drying, the material was cut in horizontal direction into three even slices by a slicer to obtain the cell supporting matrix comprising the cell support layer in the form of a porous sponge having large pores and communicating pores, and the skin layer.

2. Analysis of Large Pores, Communicating Pores and Skin Layer

[2.1] Observation with naked eye of the cell supporting matrix

Two types of the cell supporting matrix were obtained by the above-described cutting of the material (i.e. the matrix having the surface that had been in contact with the nonwoven fabric, and the matrix having no surface that had been in contact with the nonwoven fabric), and the matrix having the surface that had been in contact with the nonwoven fabric was observed with naked eye.

The surface that had been in contact with the nonwoven fabric was very dense, and smooth and no pores could be identified with naked eye. In contrast, the opposite surface (the surface which newly became exposed by the cutting with the slicer and which was originally in the interior of the material) was coarse and rough, and a large number of pores visible to the naked eye (large pores) were observed over the entire surface.

As demonstrated in the results as described above, a skin layer was formed on the surface that had been in contact with the nonwoven fabric, and the opposite surface had many large pores opening at the surface.

To confirm the observation, the matrix was analyzed as described below.

It should be noted that the surface that had been in contact with the nonwoven fabric may be referred to as the "downstream end" and the surface opposite to such surface may be referred to as the "upstream end".

[2.2] Analysis of large pores with digital scope

The cell supporting matrix was cut in horizontal direction into 8 slices by a slicer.

The end surfaces were observed with digital scope (VH-6300, manufactured by Keyence) at the magnification of 100× to 500×. The surface was observed for 5 randomly selected areas per one matrix slice.

It was then confirmed that two types of pores, namely, apparently larger pores (large pores) and apparently smaller pores (communicating pores) are formed in the cell supporting matrix. It was also confirmed by comparing the images of the slices that the size of the large pores decreases from the upstream side to the downstream side, and the number of the large pores increases from the upstream side to the downstream side.

Figure 3:
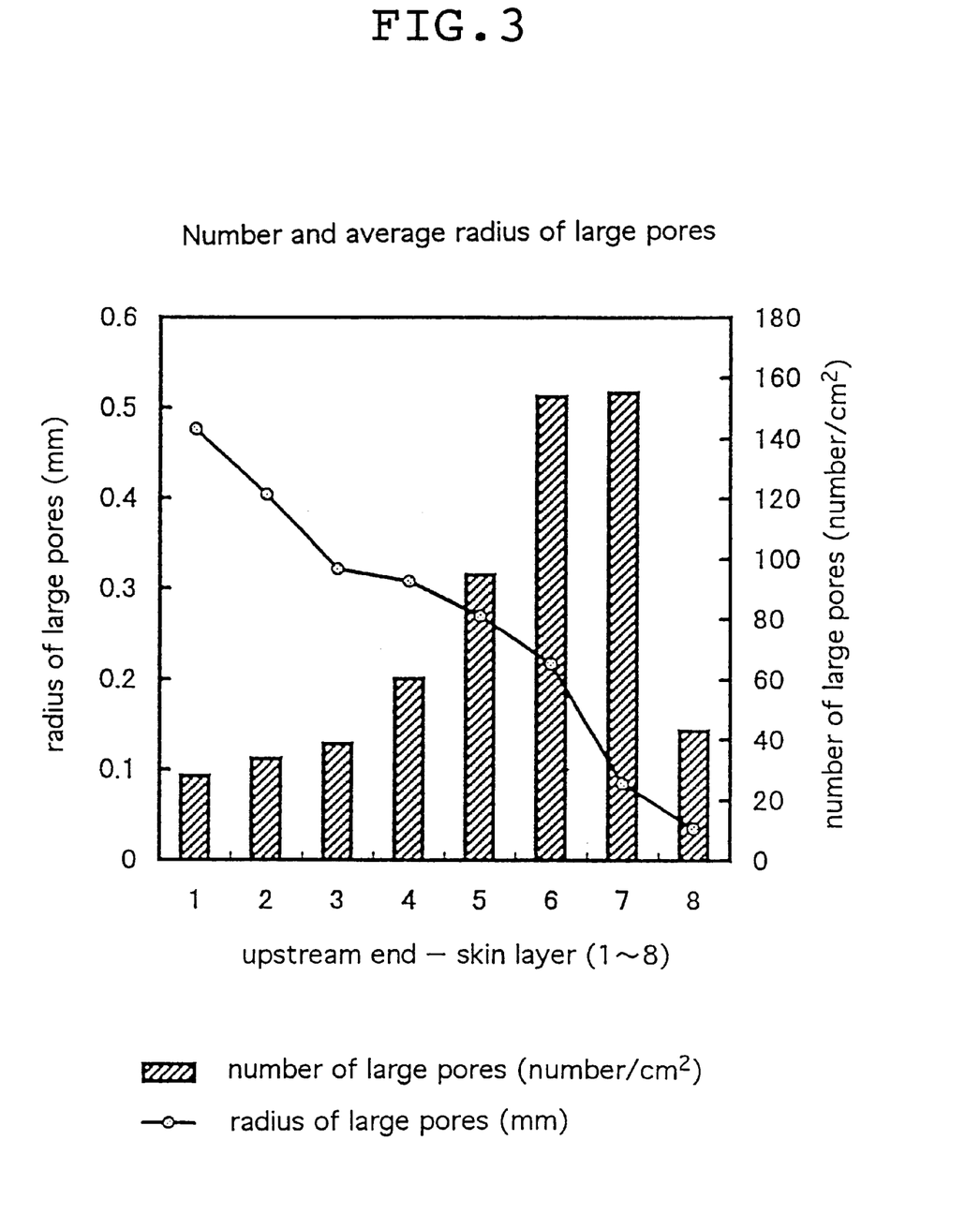
FIG. 3 is a graph showing number and average radius of the large pores found on the upstream side surface of the slices of the cell supporting matrix according to an embodiment of the present invention.

Image analysis was also conducted in the course of the observation with the digital scope to count and measure the number per 1 $cm^2$ and the average radius of the large pores formed in the upstream side surface of each slice. The results are shown in FIG. 3. In FIG. 3, the slices were numbered from the upstream side to the downstream side so that the slice on the downstream side has a larger number. Slice Nos. 1 to 7 were the part constituting the cell support layer and Slice No. 8 was the part constituting the skin layer.

As shown in the results of FIG. 3, the number of the large pores increases in the cell support layer from the upstream side to the downstream side and drastically reduces in the skin layer, indicating that the large pores are not in communication with the lower end of the matrix.

It was also demonstrated that the average radius of the large pores gradually decreases from the upstream side to the downstream side of the matrix.

The average pore size (diameter) of the large pores at the opening in the upstream end of the cell supporting matrix was 952 μm.

The average pore size (diameter) of the large pores was 530 μm.

On the bases of the data as described above, the area occupied by the large pores (per 1 $cm^2$) was calculated for each slice.

Figure 4:
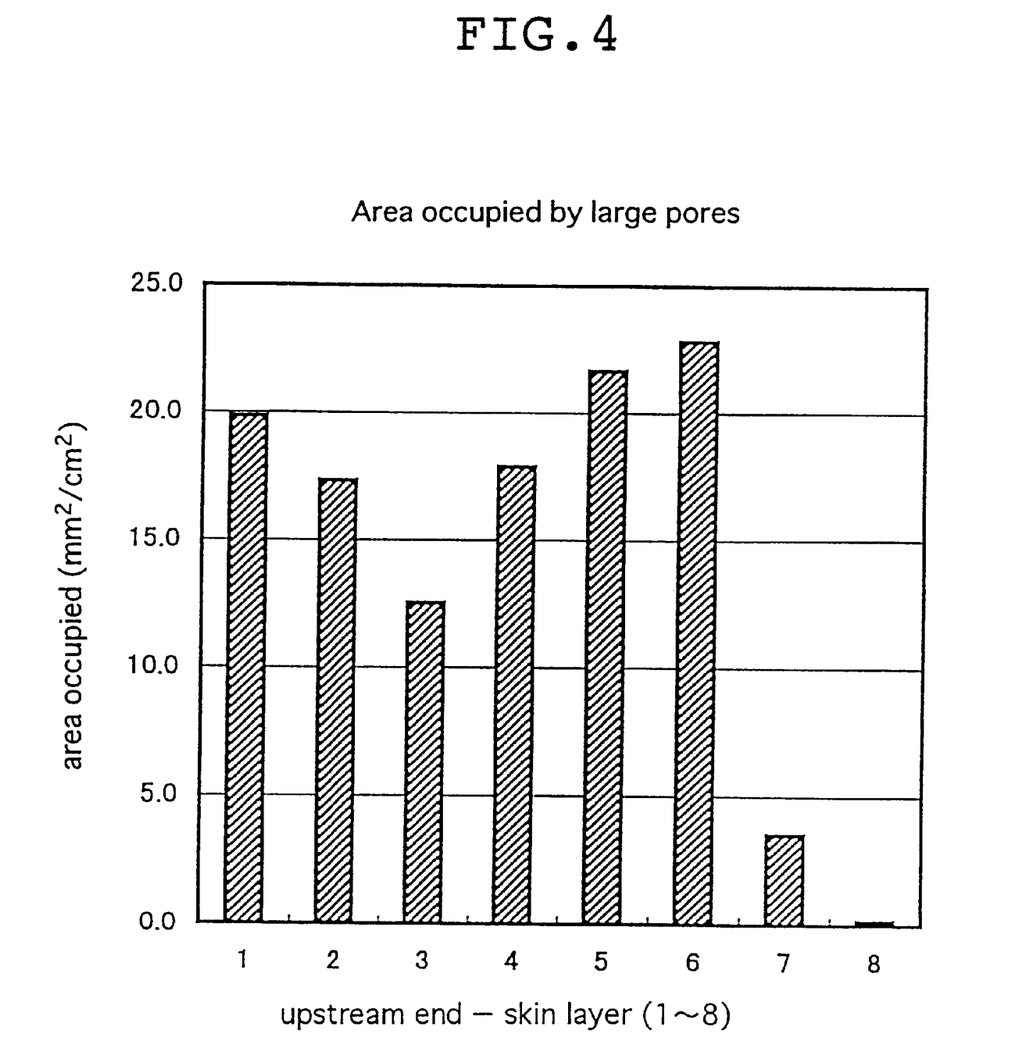
FIG. 4 is a graph showing the area occupied by the large pores in the upstream side surface of the slices of FIG. 3.

The results are shown in FIG. 4.

As shown in the results of FIG. 4, the area occupied by the large pores was quite alike in the slices of the upstream end to the second last slice of the cell support layer. The area occupied by the large pores drastically decreased in the last slice of the cell support layer, and almost no area was occupied by the large pores in the slice on the downstream end of the skin layer. It was then confirmed that the large pores do not extend to the downstream end of the matrix.

[2.3] Analysis of communicating pores with electron microscope

The cell supporting matrix was cut in horizontal direction into three slices, and samples of 0.5 mm cubes were cut out from the upstream side surface of the intermediate slice.

Gold was vapor deposited on the upstream end surface of the cubic sample by magnetron sputtering (JUC-5000, manufactured by Japan Electronics).

The surface vapor deposited with gold was observed with scanning electron microscope (JSM-840, manufactured by Japan Electronics) at a magnification of 20× to 150×.

Figure 5:
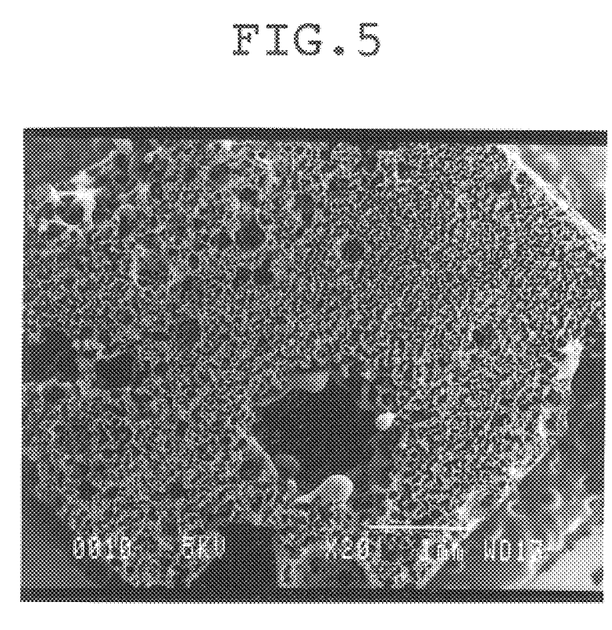
FIG. 5 is a scanning electron micrograph of the cell supporting matrix according to an embodiment of the present invention.

The resulting electron micrograph is shown in FIG. 5. FIG. 5 is a photograph of the transverse section of the cell supporting matrix.

In FIG. 5, a large pore is seen in the center slightly on the right-hand side.

As shown in FIG. 5, a large number of communicating pore is formed from the interior surface of the large pore extending in the outward direction from the large pore. It was also confirmed that the pore size reduces, namely, the pore size decreases as the communicating pore advances from the interior surface of the large pore into the interior of the matrix.

Next, this photograph was captured for image analysis on the image analyzer as described above to measure the area occupied by the communicating pores The measurement was carried out as described below.

Figure 7:
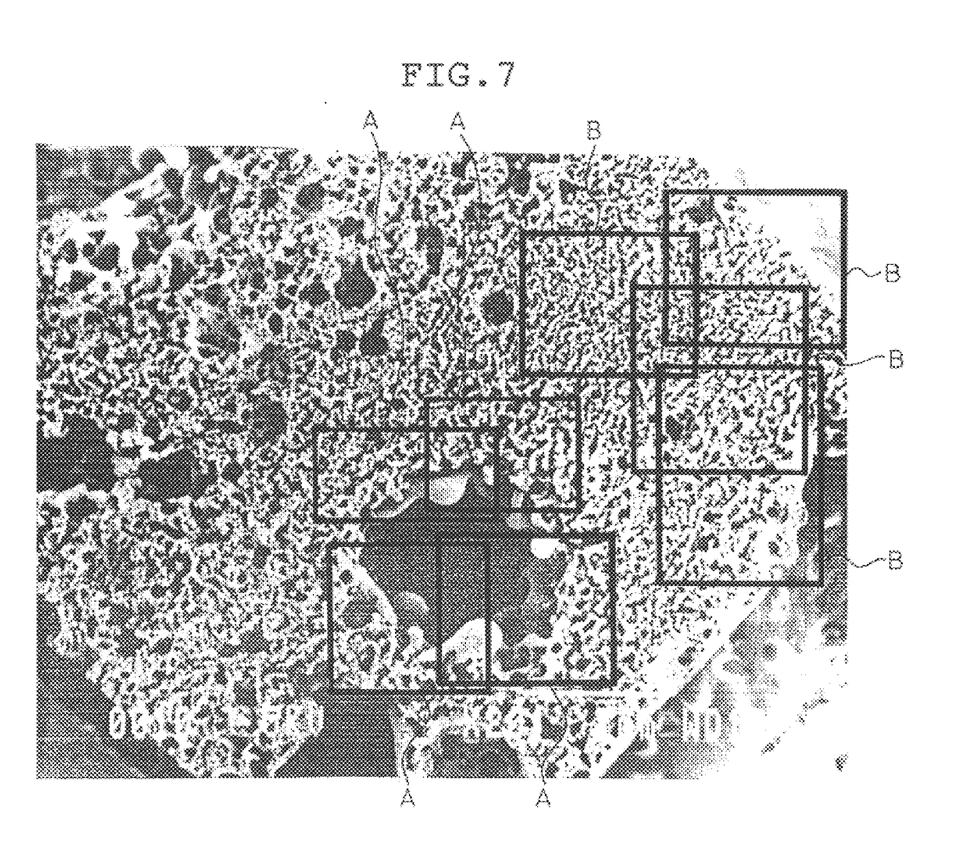
FIG. 7 is an enlarged view of FIG. 5 showing sampling regions.

(i) In the photomicrograph of FIG. 7 (which is the same as the photomicrograph of FIG. 5), four regions near the large pore (within the area of 0 to about 0.5 mm from the interior surface of the large pore) were sampled. The regions sampled are defined by square frames A.

(ii) In each of the four regions sampled, all communicating pores in the region were measured for their pore size.

(iii) Next, the communicating pores were grouped by the pore size (diameter), and the number of the communicating pores in each group was counted. The area occupied by the communicating pores was calculated for each group by using the number and the diameter of the communicating pores.

(iv) The values of the area occupied by the communicating pores of the four regions were averaged to determine the final value of the area occupied by the communicating pores for each pore diameter range.

(v) In the photomicrograph of FIG. 7, four regions remote from the large pore (within the area of about 0.5 to about 2 mm from the interior surface of the large pore) were also sampled. The regions sampled are defined by rectangular frames B. The sampled regions were measured as in the case of the regions defined by the rectangular frames A to determine the final value of the area occupied by the communicating pores for each pore diameter range.

Figure 8:
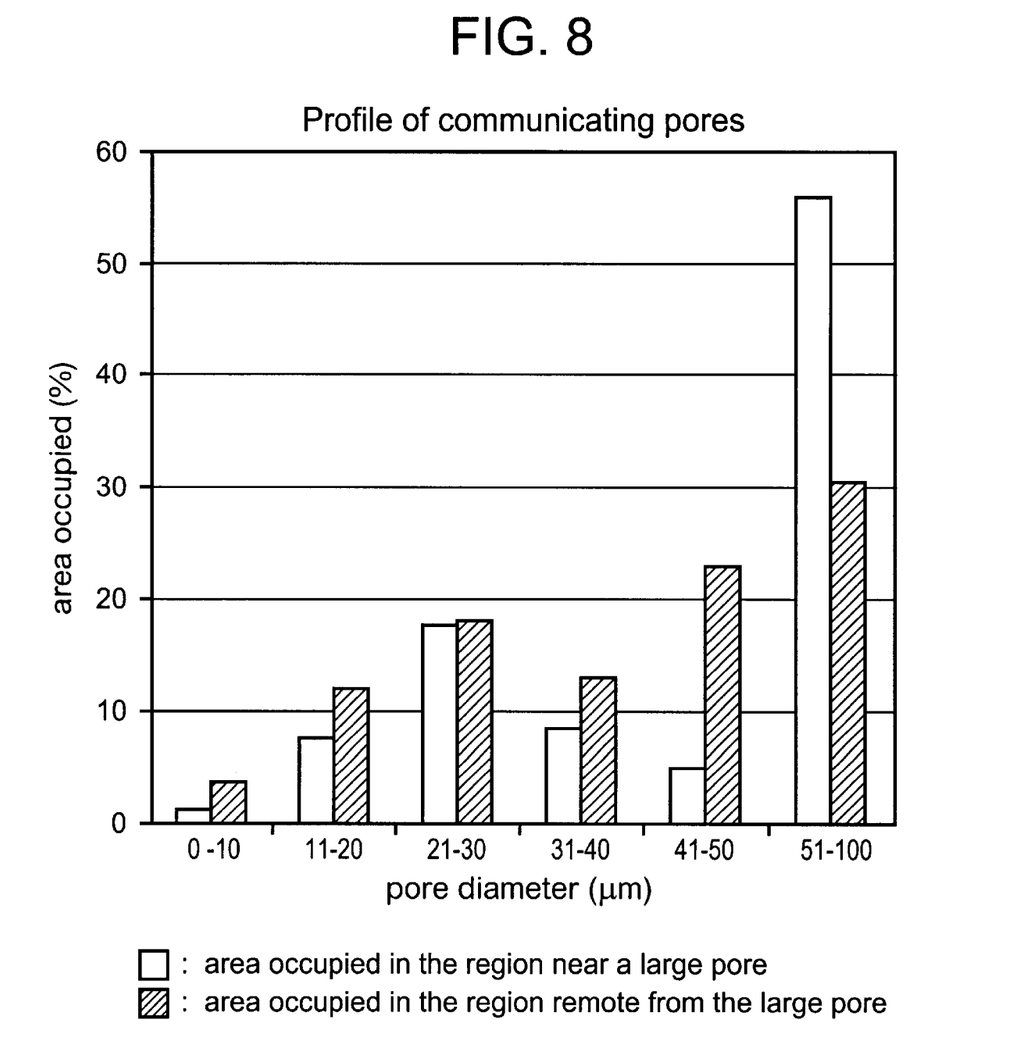
FIG. 8 is a graph showing the area occupied by the communicating pores for each pore size range both in the region near a large pore and in the region remote from the large pore in the cell supporting matrix according to an embodiment of the present invention.

The thus determined area occupied by the communicating pores for both the region near the large pore and the region remote from the large pore are shown in FIG. 8.

As shown in the results of FIG. 8, the communicating pores in the region near the large pore had a pore size profile larger than the communicating pores in the region remote from the large pore. In other words, the proportion of large size communicating pores was greater in the region near the large pore, and the proportion of small size communicating pores was greater in the region remote from the large pore.

It was then confirmed that the pore size of the communicating pore decrease from the inner surface of the large pore to the interior of the matrix.

This in turn means that the cells cultivated can easily pass through (advance into) the communicating pore in the region near the large pore because a large number of communicating pores with a lager pore diameter is present in such region, and in contrast, the cells are likely to be entrapped in the region remote from the large pore since the communicating pores of smaller pore diameter are present in such region. In other words, a good balance is maintained in the cell supporting matrix of the present invention between the communicating pores which serve the cell passage through which the cell advances into the interior of the matrix and the communicating pores in which the cells are entrapped.

From the results calculated, it was also found that the maximum size (diameter) of the communicating pores was in the range of from 51 to 142 $\mu$m; that the minimum size (diameter) of the communicating pores was in the range of from 0.5 to 10 $\mu$m; and that the average size (diameter) of the communicating pores was approximately 20 $\mu$m.

The results as described above were confirmed by changing the position of the regions analyzed. In the confirmatory analysis, the general trend was the same although the value measured were slightly different. In other words, it was further confirmed that the degree of the decrease in the pore size of the communicating pores was somewhat different by the position in the matrix.

[2.4] Observation of the skin layer with electron microscope

The surface on the downstream end of the cell supporting matrix, namely, the surface of the skin layer was observed with an electron microscope.

The observation was conducted at the same magnitude as [2.3], above, and it was then confirmed that the pores in the skin layer was obviously smaller than the communicating pores of the average pore size.

The electron micrograph of the skin layer was captured for image analysis on the image analyzer as described above to measure the average pore size of the skin layer.

The average pore size (diameter) of the skin layer was 10.55 $\mu$m.

3. Immobilization of Cells by Cell Supporting Matrix

[3.1] Preparation of the cells to be supported on the matrix

Hepatocytes (average size, 30 $\mu$m) were obtained from Wister rats having a body weight in the range of 180 to 250 g by collagenase perfusion method (see Seglen, P.O. "Methods in Cell Biology", vol. 13, page 29, 1976). The survival rate of the hepatocytes obtained was 85% or higher.

[3.2] Preparation of culture medium

To 1 liter of pure water was dissolved 10 g of Williams E medium (manufactured by GIBCO BRL) to prepare the basic medium, and a liquid culture medium was prepared by supplementing the basic medium with the substances as described below at the indicated concentration.

| | |
|---|---|
| Insulin | 10 $\mu$g/ml |
| Epidermal growth factor (EGF) | 50 ng/ml |
| Prolactin | 20 mU/ml |
| Linolenic acid | 5 $\mu$g/ml |
| $CuSO_4 \cdot 5H_2O$ | 0.1 $\mu$M |
| $H_2SeO_3$ | 3 nM |
| $ZnSO_4 \cdot 7H_2O$ | 50 pM |
| Penicillin G | 100 unit/ml |
| Streptomycin | 100 $\mu$g/ml |

[3.3] Preparation of cell supporting matrix

The cell supporting matrix prepared by repeating the procedure of [1. Production of cell supporting matrix], above was cut out in a disk shape to prepare a cell supporting matrix sample having a diameter of 30 mm and a thickness of 5.7 mm (volume, 4 cm$^3$). One surface of this cell supporting matrix sample was the surface that had been in contact with the nonwoven fabric, and the skin layer had a thickness of 0.9 mm.

Next, the cell supporting matrix was filled in a container adapted for flat membrane fixture such that liquid leakage from the outer periphery is prevented. The cell supporting matrix was then wetted with the medium prepared in [3.2], above.

[3.4] Measurement of percentage of the cells entrapped by the cell supporting matrix A 50 ml reservoir was fitted to the container having the cell supporting matrix secured thereto, and 40 ml of the hepatocyte suspension (cell density, $1.0 \times 10^6$ cells/ml) prepared in [3,1], above was allowed to flow through the cell supporting matrix by gravity. The hepatocytes were thereby filled and supported in the cell supporting matrix (number of the cells filled in the matrix: $4.0 \times 10^7$ cells; cell density: $1.0 \times 10^7$ cells per 1 cm$^3$ of the cell supporting matrix). The time required for such filling was 3 minutes.

Next, the liquid culture medium prepared in [3.2] was allowed to flow through the matrix at a flow rate of 6 ml/min for 10 minuets and the number of the cells which leaked the matrix was determined by microscopic observation with an optical microscope. The percentage of the cells leaked and the percentage of the cells entrapped were calculated from the determined value.

The measurement as described above was repeated by increasing the number of the cells filled in the matrix to $1.2 \times 10^8$ cells (cell density: $3.0 \times 10^7$ cells per 1 cm$^3$ of the cell supporting matrix).

The measurement as described was also repeated by increasing the number of the cells filled in the matrix to $2.0 \times 10^8$ cells (cell density: $5.0 \times 10^7$ cells per 1 cm$^3$ of the cell supporting matrix).

The results are shown in Tables 1 and 2, below.

TABLE 2

| | Volume of the cell supporting matrix (cm$^3$) | Number of the cells on the matrix (cells) | Percentage of the cells leaked (%) | Percentage of the cells entrapped (%) |
|---|---|---|---|---|
| 1st time | 4 | $4.0 \times 10^7$ | $(4.5 \times 10^4 / 4.0 \times 10^7) \times 100 = 0.11$ | 99.9 |
| 2nd time | 4 | $1.2 \times 10^8$ | $(2.25 \times 10^5 / 1.2 \times 10^8) \times 100 = 0.19$ | 99.8 |
| 3rd time | 4 | $2.0 \times 10^8$ | $(1.2 \times 10^5 / 2.0 \times 10^8) \times 100 = 0.06$ | 99.9 |

Figure 6:
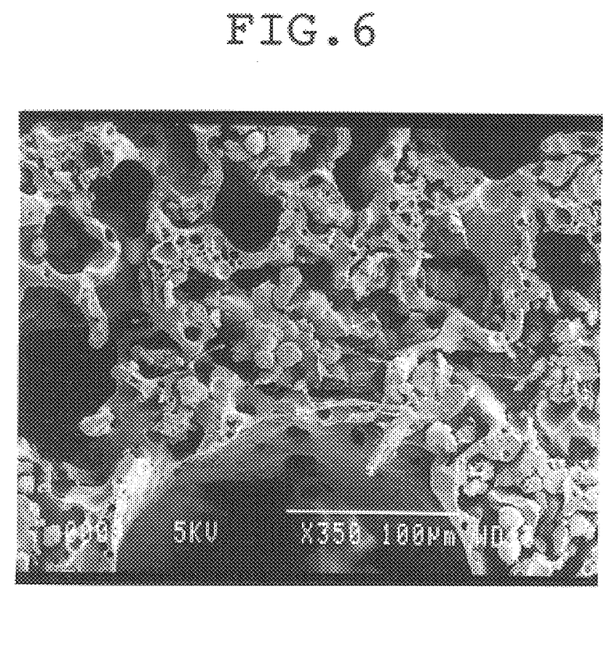
FIG. 6 is a scanning electron micrograph of the cell supporting matrix of the present invention wherein hepatocytes are supported.

The results of Tables 1 and 2 confirmed that the cell supporting matrix of the present invention is capable of supporting an extremely large number of cells at a very high density and at a high percentage of cell entrapment. [3.5] Confirmation of the state of the cells entrapped by the cell supporting matrix The cell supporting matrix having the hepatocytes filled therein prepared in [3,4] was vertically and horizontally cut into three equal slices by the slicer as described above, respectively. The cross sectional surface of the slices were observed with electron microscope as described above. One of the electron micrograph taken is shown in FIG. 6. The magnification was 350 times.

As shown in FIG. 6, it was confirmed that the hepatocytes are evenly distributed throughout the matrix without concentrating at any particular position, and that the region where the target cells are entrapped is widely distributed throughout the matrix without concentrating at any particular position.

TABLE 1

| | Time elapsed (min.) | | | | | | | |
|---|---|---|---|---|---|---|---|---|
| | 1 | 2 | 3 | 4 | 5 | 6–9 | 10 | Total |
| 1st time | | | | | | | | |
| Number of the cells escaped per 1 m | 5000 | 0 | 0 | 0 | 0 | 2500 | 0 | 7500 |
| Number of the cells escaped in the particular time period | $3.0 \times 10^4$ | 0 | 0 | 0 | 0 | $1.5 \times 10^4$ | 0 | $4.5 \times 10^4$ |
| 2nd time | | | | | | | | |
| Number of the cells escaped per 1 ml | $2.25 \times 10^4$ | $0.75 \times 10^4$ | 0 | $0.25 \times 10^4$ | $0.5 \times 10^4$ | 0 | 0 | $3.75 \times 10^4$ |
| Number of the cells escaped in the particular time period | $1.35 \times 10^5$ | $4.5 \times 10^4$ | 0 | $1.5 \times 10^4$ | $3.0 \times 10^4$ | 0 | 0 | $2.25 \times 10^5$ |
| 3rd time | | | | | | | | |
| Number of the cells escaped per 1 ml | 2500 | 2500 | 5000 | 2500 | 2500 | 5000 | 0 | $2.0 \times 10^4$ |
| Number of the cells escaped in the particular time period | $1.5 \times 10^4$ | $1.5 \times 10^4$ | $3.0 \times 10^4$ | $1.5 \times 10^4$ | $1.5 \times 10^4$ | $3.0 \times 10^4$ | 0 | $1.2 \times 10^5$ |

4. Cell Culture Device

[4.1] Cultivation of hepatocytes

Hepatocytes were filled and supported in the cell supporting matrix to a final cell density of $1\times10^7$ cells/cm by repeating the procedure of [3. Supporting of cells by cell supporting matrix], above.

The hepatocytes were then cultured in a cell culture device as shown in FIG. 2.

The perfusate used was 50 ml of the liquid culture medium prepared as described in [3.2], above, and the perfusate was allowed to flow at a flow rate of 6 ml/min. A gas mixture comprising 95% oxygen ($O_2$) and 5% carbon dioxide ($CO_2$) was allowed to flow through gas addition means (an oxygenator) at a flow rate of 200 ml/min to oxygenate the perfusate. The oxygenator used had a hollow fiber membrane area of 0.03 $m^2$.

The half of the medium was replaced every 12 hours.

The hepatocytes were confirmed to be alive and active after 5 days. It was then demonstrated that cultivation of an attachment animal cell whose cultivation had been difficult has been enabled by the cell culture device employing the cell supporting matrix of the present invention.

[4.2] Percentage of the hepatocytes immobilized in the cell culture the device.

Hepatocytes were filled and supported in the cell supporting matrix to a final cell density of $1\times10^7$ cells/$cm^3$ by repeating the procedure of [3. Supporting of cells by cell supporting matrix], above.

The thus prepared matrix was filled in the cell culture device as in the case of [4.1], above.

A perfusate was allowed to flow through the matrix at a flow rate of 5 ml/min for 24 hours as in the case of [4.1], above. The perfusate used was 50 ml of the liquid culture medium prepared as described in [3.2], above.

The liquid culture medium which had been used as the perfusate was measured by repeating the procedure of [3.4], above to determine the percentage of cell immobilization after the starting of the operation of the cell culture device.

The percentage of cell immobilization was 99.9% or higher, and it was then confirmed that the cell culture device has extremely high percentage of cell immobilization.

5. Bioartificial Liver

The device described in [4.1], above was also used for a bioartificial liver.

The perfusate used was the liquid culture medium prepared as described in [3.2], above, and half of the perfusate was replaced with fresh perfusate every 12 hours.

The culture medium collected in the replacement was assayed for albumin concentration by ELISA (enzyme-linked immunosorbent assay) to determine the amount of the albumin produced (secreted) by the hepatocytes. Capacity of the device as a bioartificial liver was thereby evaluated.

Figure 9:
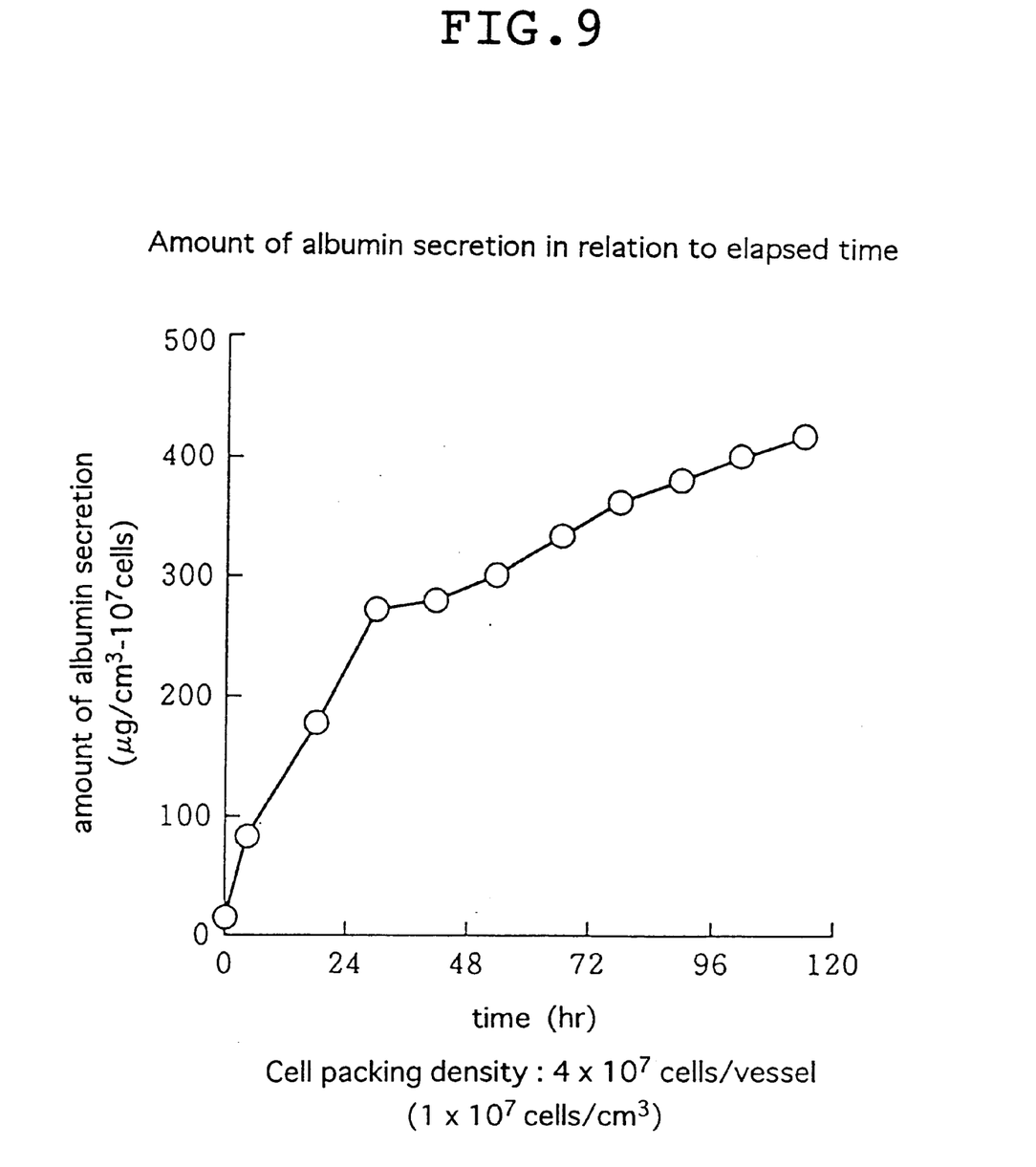
FIG. 9 is a graph showing amount of albumin secretion in the bioartificial liver in relation to the time elapsed.

Amount of the albumin secretion per 1 $cm^3$ of the cell supporting matrix (i.e. per $1\times10^7$ hepatocytes) is depicted in FIG. 9 in relation to time.

As shown in FIG. 9, the hepatocytes immobilized on the cell supporting matrix were confirmed to secrete the albumin for 5 days after the start of the perfusion.

It was then confirmed that the device was functioning as a bioartificial liver.

It should be noted that the device used as the bioartificial liver is estimated to exhibit an extremely high percentage of cell immobilization in consideration of the results of [4.2], above.

As described above, the cell supporting matrix of the present invention is capable of supporting the cells in a simple manner, and in a quite short time.

In addition, the cell supporting matrix of the present invention is capable of supporting the target cells at a high percentage of entrapment, and at a high percentage of immobilization.

Furthermore, the cell supporting matrix of the present invention is capable of supporting the cells uniformly, and at a high density.

Still further, the cell supporting matrix of the present invention has enabled to cultivate the attachment animal cells whose cultivation has been difficult by conventional matrix, and therefore, the cell supporting matrix of the present invention has a wide variety of applications.

In consideration of such advantageous features, the cell supporting matrix of the present invention can be used in a cell culture device and in a fluid treating device such as a bioartificial organ, and the cell culture device and the fluid treating device thus provided has excellent performance, efficiency and safety.

What is claimed is:

1. A matrix for supporting cells having an upstream surface, a downstream surface and thickness between them, said matrix having formed therein a plurality of cone shaped pores along the thickness of the matrix, wherein an average pore diameter of an opening of said cone shaped pores in the upstream surface ranges from 500 to 1500 $\mu$m, said pore diameter decreases from the upstream surface to the downstream surface, and the average pore diameter of the cone shaped pores in the whole matrix ranges from 100 to 1000 $\mu$m, and a plurality of communicating pores communicating with the cone shaped pores and with each other, having an average diameter ranging from 5 to 100 $\mu$m and the diameter of the communicating pores decreases from a pore opening positioned near one surface of the matrix or near an interior surface of said cone shaped pores to a pore opening positioned remote from said surfaces.

2. The matrix of claim 1, wherein said matrix further comprises a plurality of column shaped pores along the thickness of the matrix where the average pore diameter of the column shaped pores in the whole matrix ranges from 100 to 1000 $\mu$m.

3. A matrix for supporting cells according to claim 1, wherein the average pore diameter in the whole matrix of the cone shaped pores ranges from 100 to 500 $\mu$m and the average pore diameter of the communicating pores ranges from 10 to 70 $\mu$m.

4. A matrix for supporting cells according to claim 1, wherein said matrix comprises polyurethane.

5. A matrix for supporting cells according to claim 1, wherein said matrix further comprises a porous skin layer disposed on said downstream surface of the matrix.

6. A matrix for supporting cells according to claim 5, wherein said skin layer has an average pore size smaller than said average pore size of said communicating pores.

7. A matrix for supporting cells according to claim 1, wherein said matrix has elasticity.

8. A matrix for supporting cells according to claim 1, wherein said cells are animal cells.

9. A device for cell culture or for treating a fluid comprising a cell supporting module containing the matrix for supporting cells of claim 1.

* * * * *